United States Patent
Salehi

(10) Patent No.: US 10,130,376 B2
(45) Date of Patent: Nov. 20, 2018

(54) SELF-CLEANING TISSUE REMOVAL INSTRUMENT AND METHOD OF USE

(71) Applicant: NEUROENTERPRISES, LLC, Port Barrington, IL (US)

(72) Inventor: Sean A. Salehi, Chicago, IL (US)

(73) Assignee: NEUROENTERPRISES, LLC, Chicago, IL (US)

(*) Notice: Subject to any disclaimer, the term of this patent is extended or adjusted under 35 U.S.C. 154(b) by 699 days.

(21) Appl. No.: 14/697,176

(22) Filed: Apr. 27, 2015

(65) Prior Publication Data

US 2015/0305820 A1    Oct. 29, 2015

Related U.S. Application Data

(60) Provisional application No. 61/995,939, filed on Apr. 25, 2014.

(51) Int. Cl.
*A61B 17/16* (2006.01)
*A61B 19/00* (2006.01)
(Continued)

(52) U.S. Cl.
CPC .......... *A61B 17/1611* (2013.01); *A61B 90/70* (2016.02); *A61B 17/1606* (2013.01);
(Continued)

(58) Field of Classification Search
CPC ............ A61B 17/1604; A61B 17/1606; A61B 17/1611; A61B 17/160829;
(Continued)

(56) References Cited

U.S. PATENT DOCUMENTS

| | | | |
|---|---|---|---|
| 5,925,050 A | * | 7/1999 | Howard, III ....... A61B 17/1604 606/83 |
| 2011/0213369 A1 | | 9/2011 | Weaver .......................... 606/83 |

(Continued)

FOREIGN PATENT DOCUMENTS

WO    WO 2009/141318    11/2009    ............. A61B 17/16

OTHER PUBLICATIONS

Boss Instruments Ltd. Kerrison & IVD Rongeurs. 2013, precisionsurgical.co.uk/wp-content/uploads/2017/02/Boss_Kerrison-IVD_May2013.compressed.pdf. accessed on Mar. 9, 2018.*

(Continued)

*Primary Examiner* — Eric S Gibson
*Assistant Examiner* — Marcela I Shirsat
(74) *Attorney, Agent, or Firm* — J. Peter Paredes; David G. Rosenbaum; Rosenbaum IP, P.C.

(57) ABSTRACT

A self-cleaning tissue removal instrument is disclosed and described herein. The self-cleaning tissue removal instrument generally comprising: a handle operably coupled with a proximal end of a rail portion; a jaw portion operably coupled to a distal end of the rail portion, a longitudinal axis running along the proximal portion to the distal portion of the self-cleaning tissue removal instrument; wherein the jaw portion is moved from an open position to a closed position by operation of the rail portion translating along the longitudinal axis of the self-cleaning tissue removal instrument, and the jaw portion clamps down and removes tissue in the closed position; and a cleaning mechanism operably coupled with the rail portion, whereby the cleaning mechanism disengages any tissue attached to the jaw portion when the jaw portion longitudinally translates to the open position.

10 Claims, 15 Drawing Sheets

(51) Int. Cl.
*A61B 90/70* (2016.01)
*A61B 17/29* (2006.01)
*A61B 18/14* (2006.01)
*A61B 17/32* (2006.01)

(52) U.S. Cl.
CPC ........... *A61B 17/32* (2013.01); *A61B 18/1445* (2013.01); *A61B 2017/2905* (2013.01)

(58) Field of Classification Search
CPC ............ A61B 17/07207; A61B 17/068; A61B 17/072; A61B 17/115; A61B 17/32; A61B 90/70; A61B 18/1445; A61B 2017/07257; A61B 2017/07214; A61B 2017/07278; A61B 2017/2905; B26B 19/066; B26B 17/02; B26B 17/003; B26B 13/26; B26B 13/16; B23D 29/023
USPC ....... 600/562, 564, 566–567; 606/79, 83–84, 606/90, 99, 110, 167, 168, 170, 172, 174, 606/184, 205–210, 246; 30/113.1, 113.2, 30/113.3, 182, 184, 214, 242; 227/180.1
See application file for complete search history.

(56) References Cited

U.S. PATENT DOCUMENTS

2013/0245613 A1 9/2013 Salehi et al. .................. 604/540
2016/0135817 A1* 5/2016 Kerboul et al. ... A61B 17/1604
606/83

OTHER PUBLICATIONS

International Search Report issued in corresponding foreign application, PCT/US2015/027795, pp. 1-3 (dated Aug. 27, 2015).
Written Opinion issued in corresponding foreign application, PCT/US2015/027795, pp. 1-4 (dated Aug. 27, 2015).

* cited by examiner

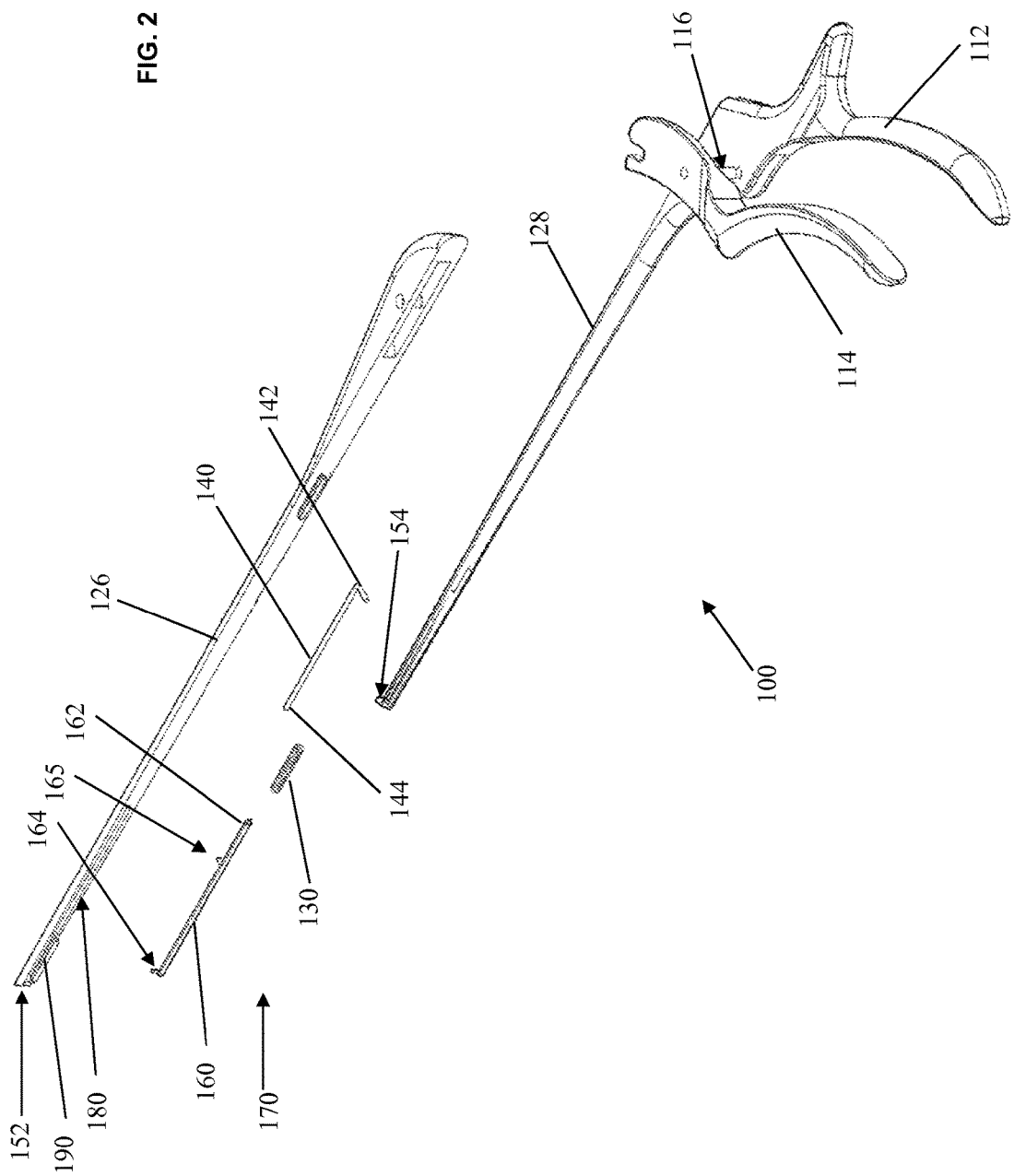

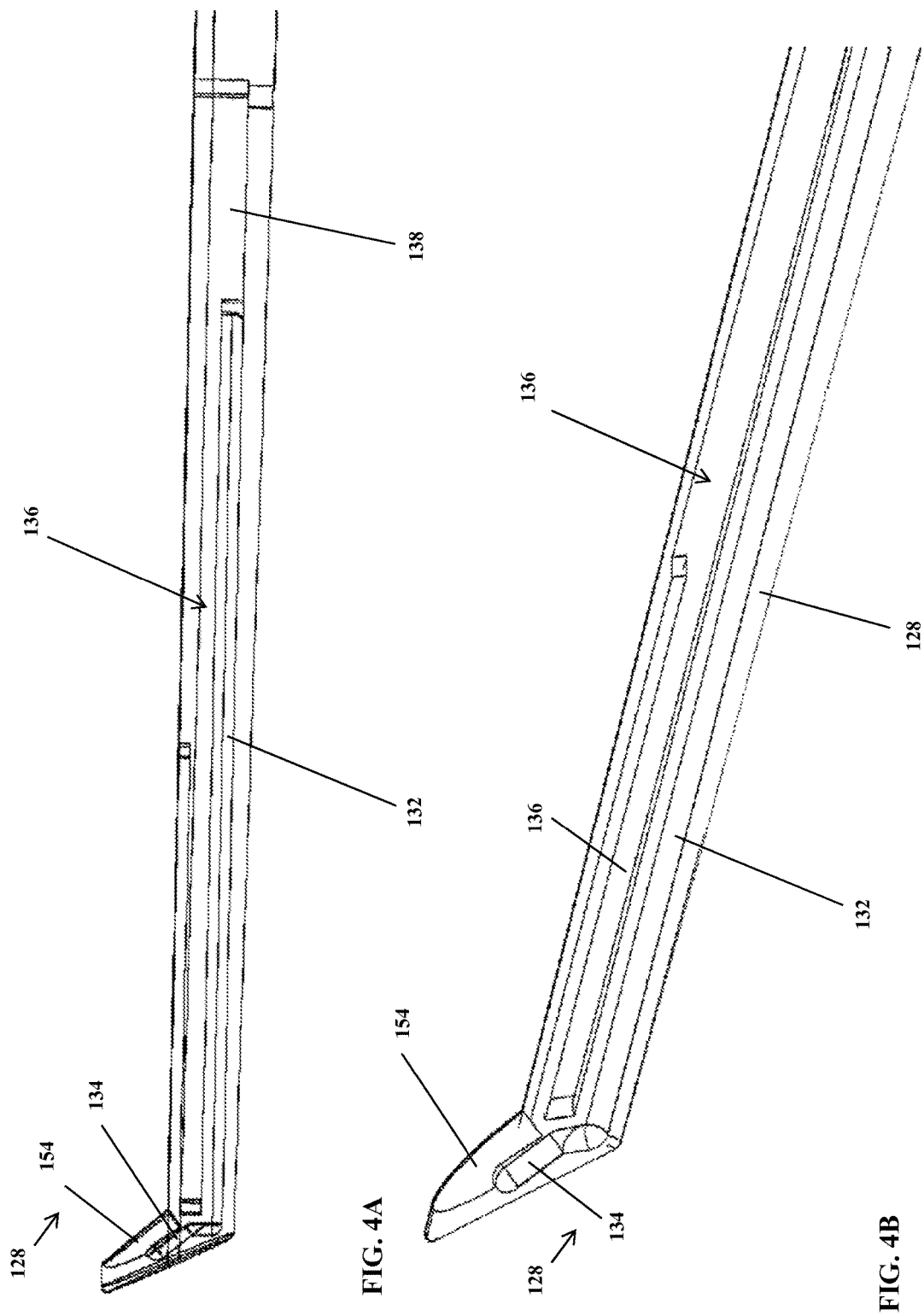

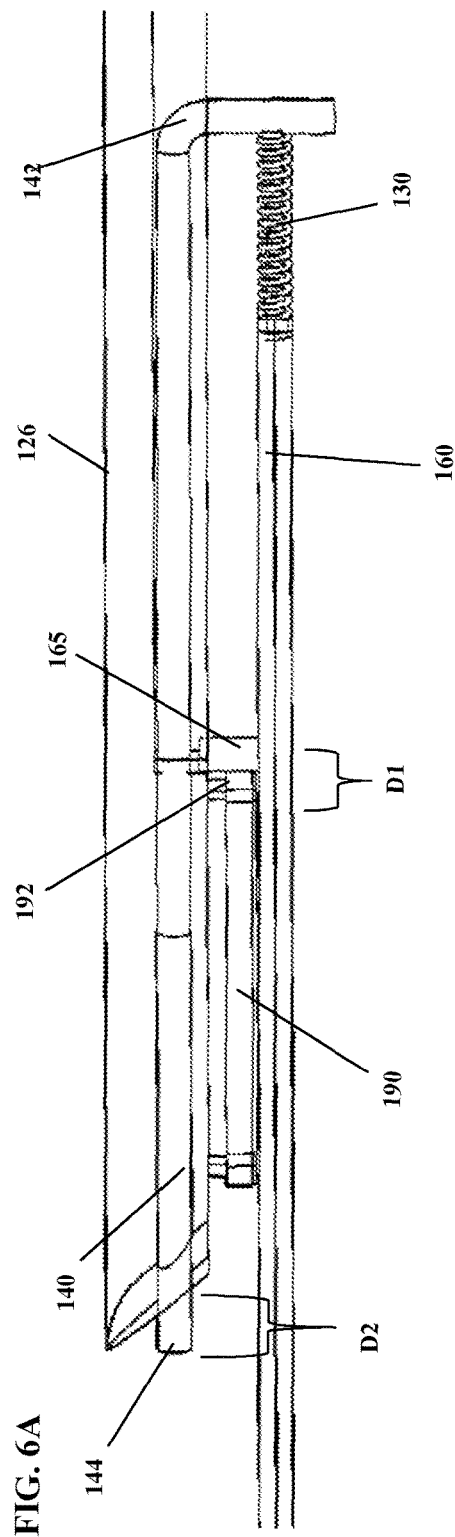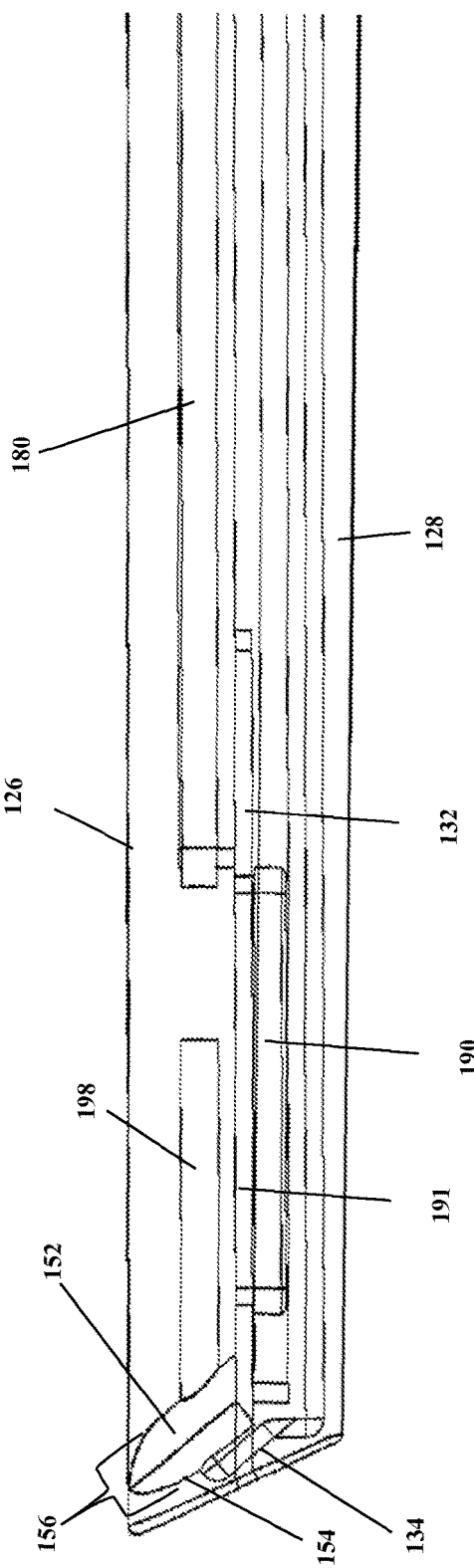
FIG. 6A
FIG. 6B

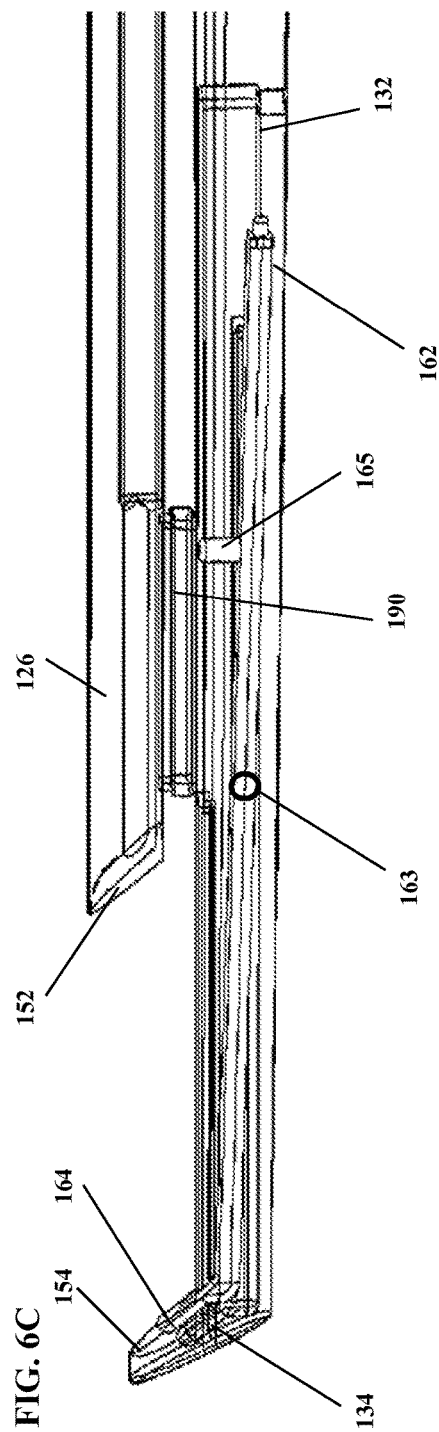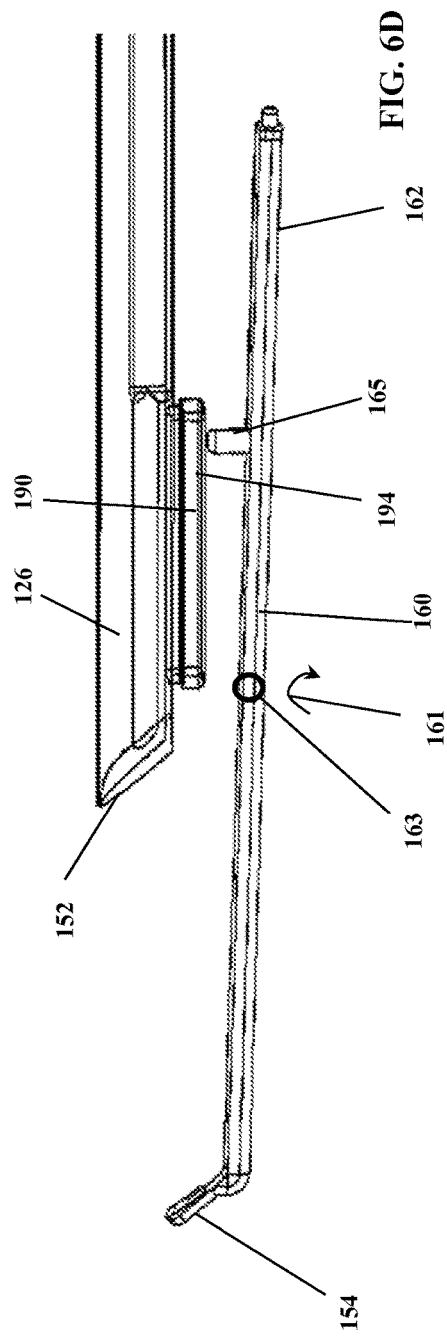

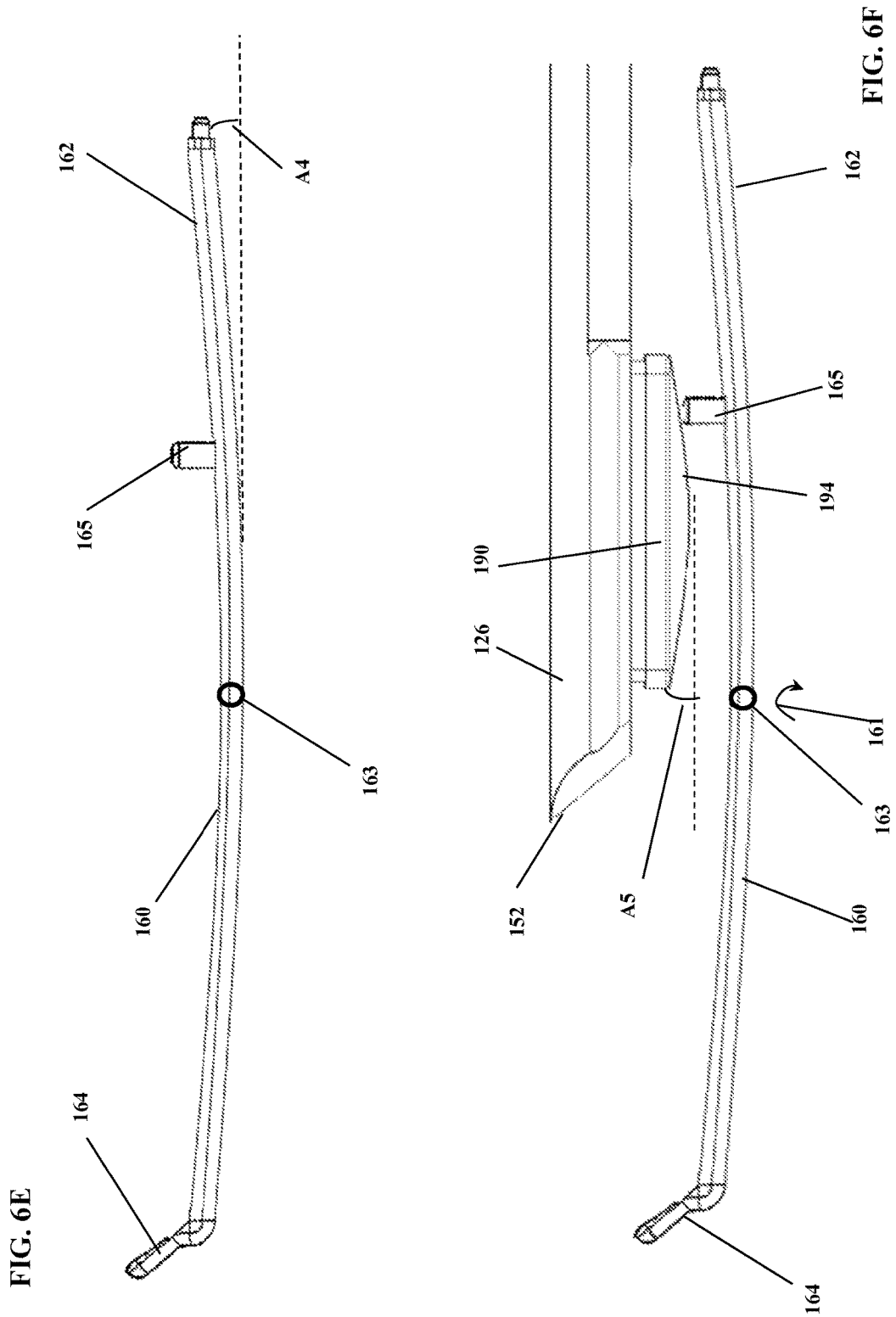

FIG. 7C
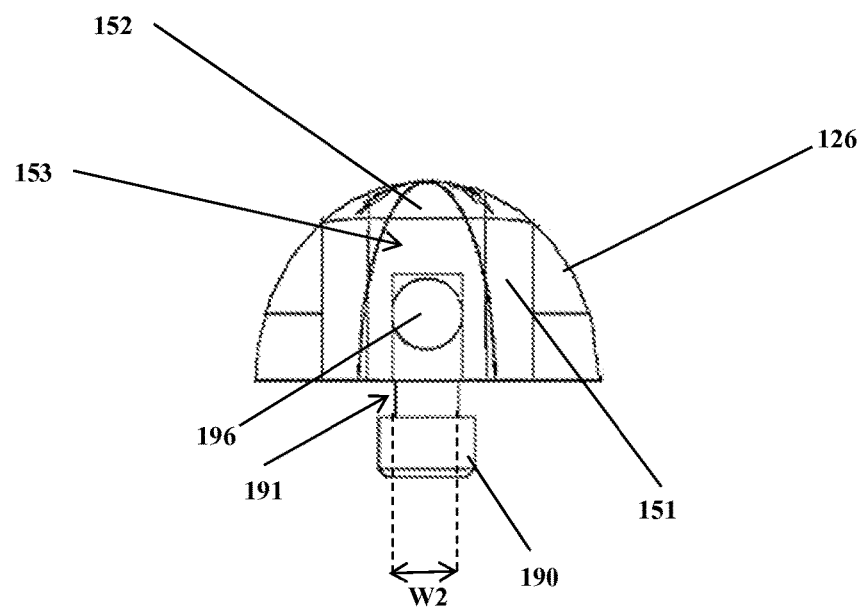
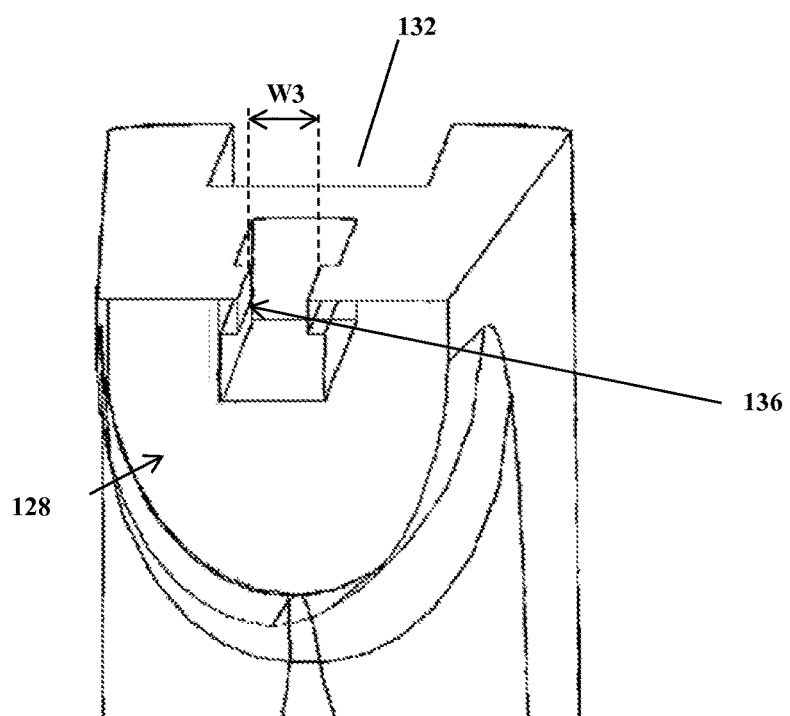
FIG. 7D

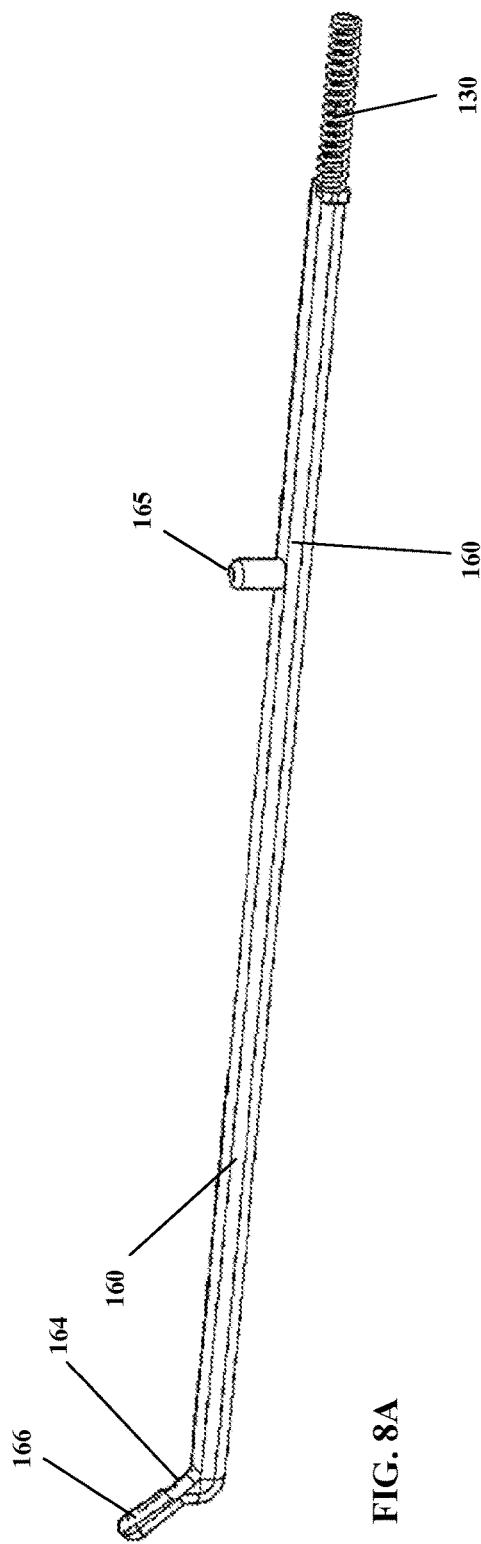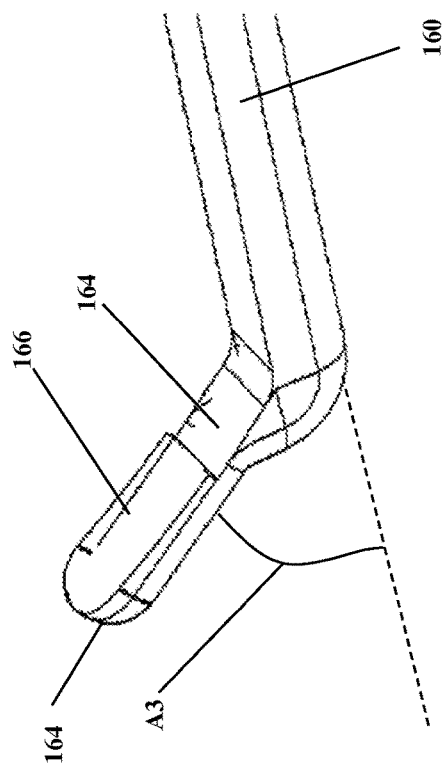
FIG. 8A
FIG. 8B

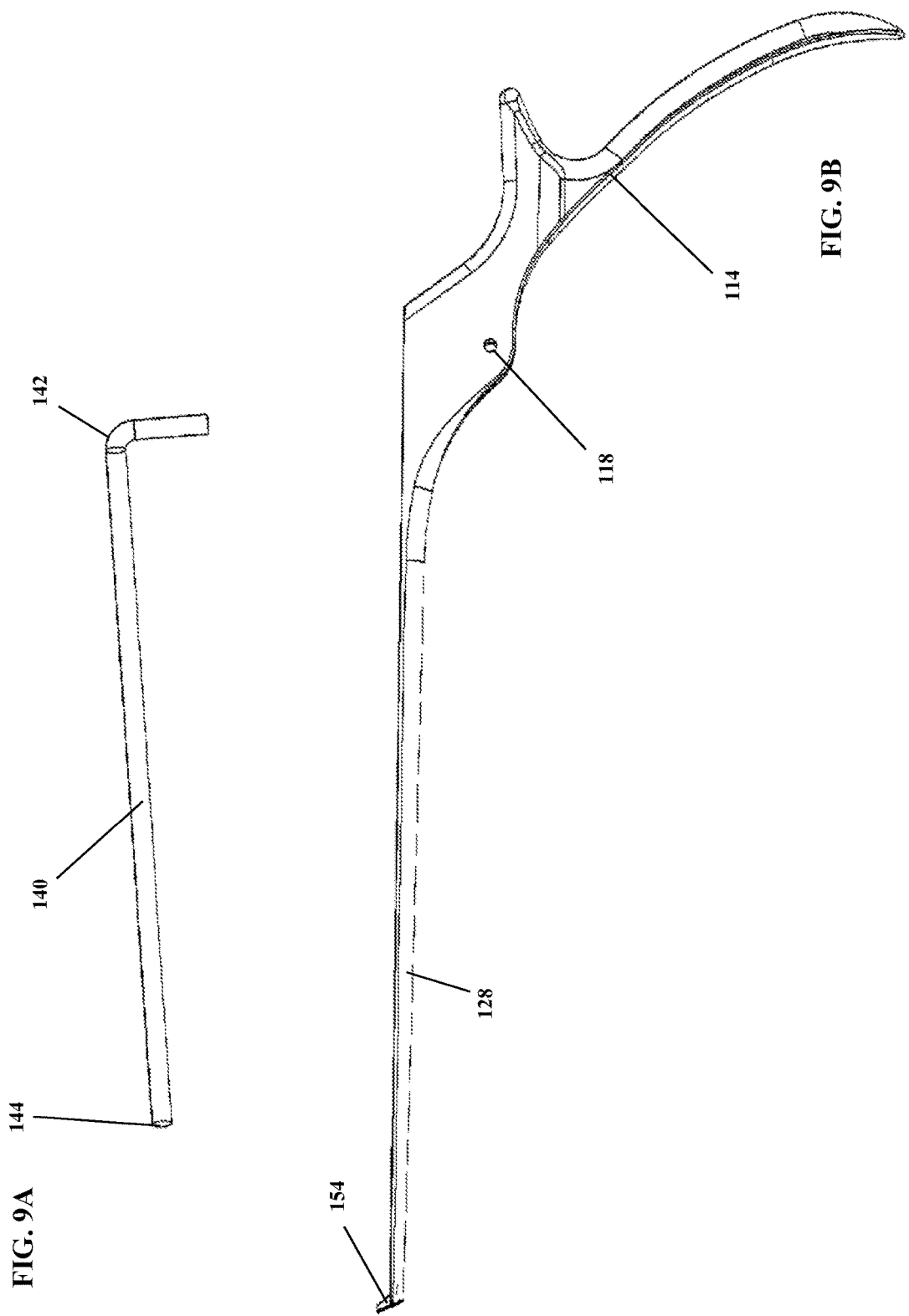

SELF-CLEANING TISSUE REMOVAL INSTRUMENT AND METHOD OF USE

CROSS-REFERENCE TO RELATED APPLICATIONS

The present application claims priority from U.S. Provisional Application Ser. No. 61/995,939, filed Apr. 25, 2014, herein incorporated by reference in its entirety.

BACKGROUND

The present invention relates generally to tissue removal devices and, more particularly, to rongeurs and methods for removing tissue.

Spinal decompression for spinal stenosis is accomplished using a high speed drill and Kerrison punches and rongeurs. A kerrison punch is used to remove the lamina and ligamentum flavum. The punched material is then cleaned by an assistant to the surgeon using a sponge before the next punch. Cleaning the instrument is time consuming and the cleaning process at times does not happen to full extent. The present invention attempts to solve this problem, as well as others.

SUMMARY OF THE INVENTION

Provided herein are systems, methods and apparatuses for a self-cleaning tissue removal instrument generally comprising: a handle operably coupled with a proximal end of a rail portion; a jaw portion operably coupled to a distal end of the rail portion, a longitudinal axis running along the proximal portion to the distal portion of the self-cleaning tissue removal instrument; wherein the jaw portion is moved from an open position to a closed position by operation of the rail portion translating along the longitudinal axis of the self-cleaning tissue removal instrument, and the jaw portion clamps down and removes tissue in the closed position; and a cleaning mechanism operably coupled with the rail portion, whereby the cleaning mechanism disengages any tissue attached to the jaw portion when the jaw portion longitudinally translates to the open position.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 2 is an exploded perspective view of the self-cleaning tissue removal instrument.

FIG. 4A is a side view of the bottom rail portion shown in phantom, showing the seated recess, the rail portion and the groove portion.

FIG. 4B is a perspective view of a cross-section of the bottom rail portion.

FIG. 6A is a side view of the top rail portion shown in phantom and the rod disposed within the top rail portion and the ejector coupled with the rod and the top rail portion.

FIG. 6B is a side view of the top rail portion shown in phantom and the bottom rail portion shown in phantom in the closed position.

FIG. 6C is a side view of the top rail portion shown in phantom and the bottom rail portion shown in phantom in the open position for an alternative embodiment.

FIG. 6D is a side view of the top rail portion shown in phantom engaged with the ejector in the open position and the bottom rail portion removed for an alternative embodiment.

FIG. 6E is a side view of an alternative embodiment of the ejector with a curvature along its longitudinal axis.

FIG. 6F is a side view of the top rail portion shown in phantom engaged with the ejector in the open position and the bottom rail portion removed for an alternative embodiment.

FIG. 7C is a cross-sectional view of the top rail portion.

FIG. 7D is a cross-sectional view of the bottom rail portion.

FIG. 8A is a perspective view of the ejector.

FIG. 8B is a perspective view of the distal end of the ejector.

FIG. 9A is a side view of the rod.

FIG. 9B is a side view of the second handle and the bottom rail portion.

DETAILED DESCRIPTION OF THE INVENTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient.

The use of the terms "a" and "an" and "the" and similar referents in the context of describing the invention are to be construed to cover both the singular and the plural, unless otherwise indicated herein or clearly contradicted by context.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The self-cleaning tissue removal instrument may be used in arthroscopic, orthopedic, or endoscopic surgery to remove or treat human tissue. In one embodiment, the self-cleaning tissue removal instrument operates as a Kerrison Punch Rongeur to remove tissue. In one embodiment, the self-cleaning tissue removal instrument is used to remove the lamina and ligamentum flavum; however, other tissue may be removed by the self-cleaning tissue removal instrument.

Figure 1A:
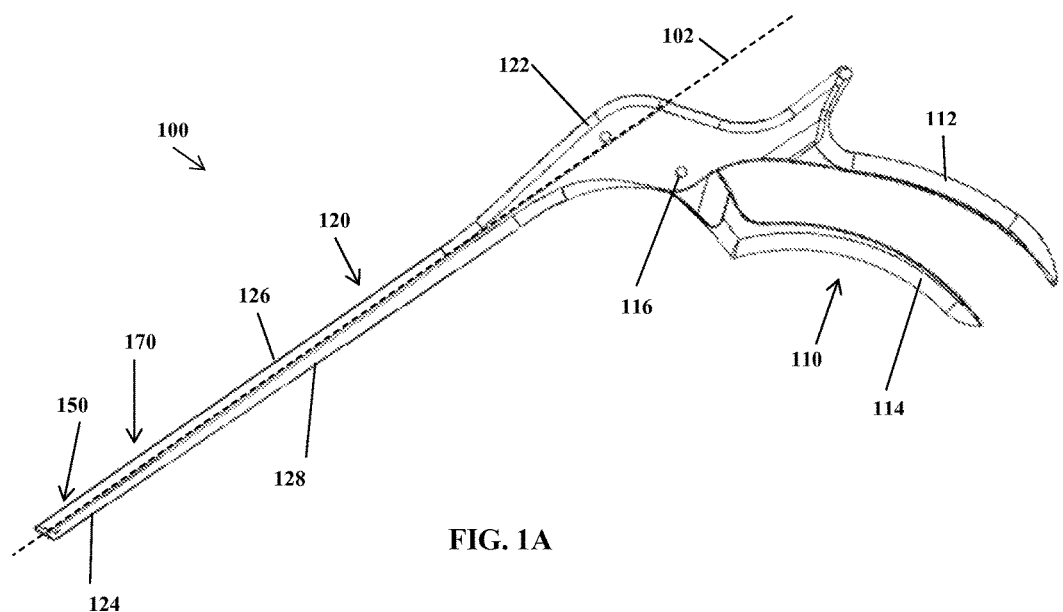
FIG. 1A is a perspective view of the self-cleaning tissue removal instrument in the closed position.
Figure 1B:
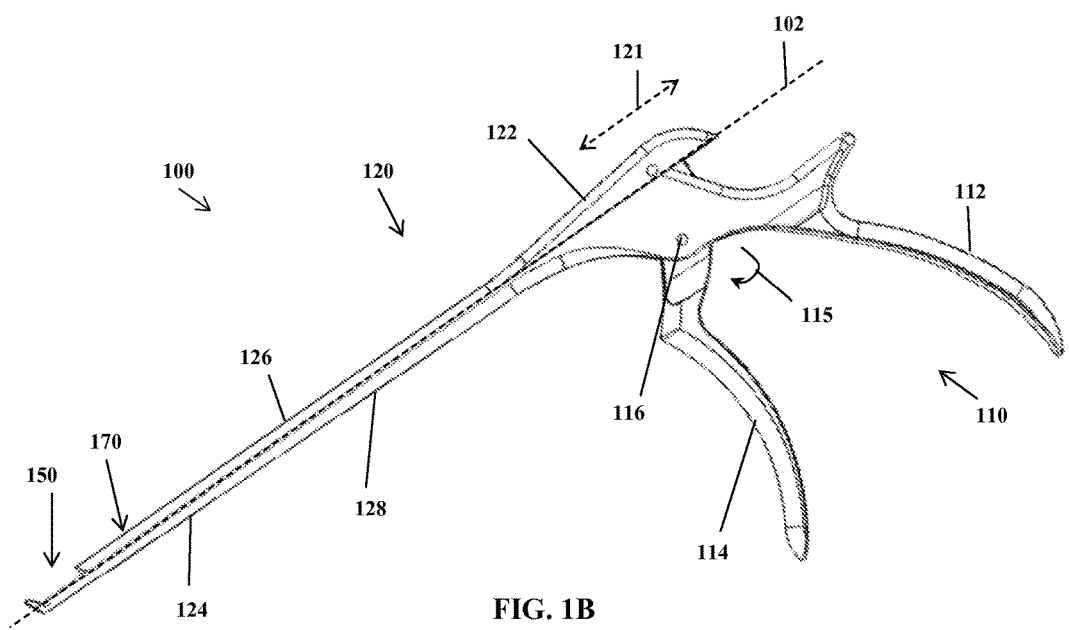
FIG. 1B is a perspective view of the self-cleaning tissue removal instrument in the open position.

Generally speaking, the self-cleaning tissue removal instrument 100 generally comprises a handle 110 operably coupled with a proximal end 122 of a rail portion 120 and a jaw portion 150 operably coupled to a distal end of 124 the rail portion 120, as shown in FIG. 1A. The self-cleaning tissue removal instrument 100 generally includes a longitudinal axis 102 running along the proximal portion to the distal portion of the self-cleaning tissue removal instrument 100. The jaw portion 150 is moved from an open position to a closed position and to the open position from the closed position by operation of the rail portion 120 translating or moving along the longitudinal axis of the self-cleaning tissue removal instrument 100. The rail portion 120 includes a top rail portion 126 operably coupled with a bottom rail portion 128. The self-cleaning tissue removal instrument 100 includes a cleaning mechanism 170 generally coupled with the top rail portion 126 and the bottom rail portion 128, whereby the top rail portion 126 longitudinally translates in the direction of arrow 121 along the longitudinal axis 102 to the clean or disengage any tissue stuck or attached to the jaw portion 150, as shown in FIG. 1B. The jaw portion 150 is in the closed position is shown in FIG. 1A, whereby the jaw portion 150 longitudinally translates to the closed position to clamp down and remove tissue as needed by an operator. The handle 110 operates to open the jaw portion 150 and longitudinally translate the top rail portion 126 from the open position to the closed position. The handle 110 includes a first handle 112 rotatably coupled with a second handle 114 by way of a pin 116. The first handle 112 is operably coupled with the bottom rail portion 128 and the second handle 114 is operably coupled with the top rail portion 126. The second handle 114 rotates about the first handle 112 in the direction of arrow 115 as to longitudinally translate the top rail portion 126 in the direction of arrow 121, which then opens the jaw portion 150, as further described below. In one embodiment, the second handle 114 biases to the top rail portion 126 towards to the open position. Alternatively, the second handle 114 biases the top rail portion 126 towards to the closed position.

As shown in FIG. 2, the cleaning mechanism 170 generally includes an ejector 160 operably coupled with the distal end of the bottom rail portion 128, a spring 130 operably coupled to a proximal end 162 of the ejector 160, and a rod 140 operably coupled with the distal end of the top rail portion 126. The ejector 160 and the rod 140 operate to remove or detach tissue disposed within the jaw portion 150. The ejector 160 includes a cleaning post 164 on the distal end to remove or detach punched tissue from the jaw portion 150. The rod 140 includes a proximal end 142 with a substantially right angle and a distal end 144. The top rail portion 126 includes a grooved inner surface 180 as to receive the rod 140 and to allow the top rail portion 126 to longitudinally translate along the rod 140. The top rail portion 126 includes a distal lip portion 190 to engage the bottom rail portion 128 and to be able to longitudinally translate on top of the bottom rail portion 128. The top rail portion 126 longitudinally translate in a railway fashion with respect to the bottom rail portion 128, whereby the bottom rail portion 128 remains substantially stationary with respect to the top rail portion 126. Although the top rail portion 126 longitudinally translates on top of the bottom rail portion 128, the top rail portion 126 may be operably coupled on any axial side of bottom rail portion 128. For example, the top rail portion 126 may longitudinal translate on the right side, the left side, or the bottom side of the bottom rail portion 128. As such, "top" and "bottom" are used herein only for exemplary purposes for describing an embodiment of the self-cleaning tissue removal instrument 100. The ejector 160 includes a pin 165 disposed on the middle portion of the ejector 160. In one embodiment, the pin 165 is disposed on the ejector at a substantially right angle.

Figure 3A:
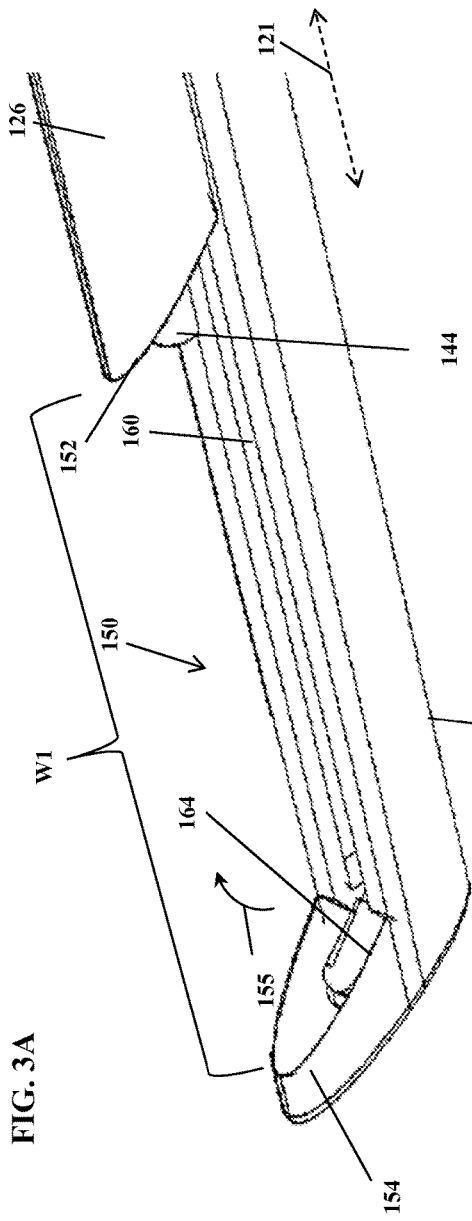
FIG. 3A is a perspective view of the top rail portion and the bottom rail portion in the open position.
Figure 3B:
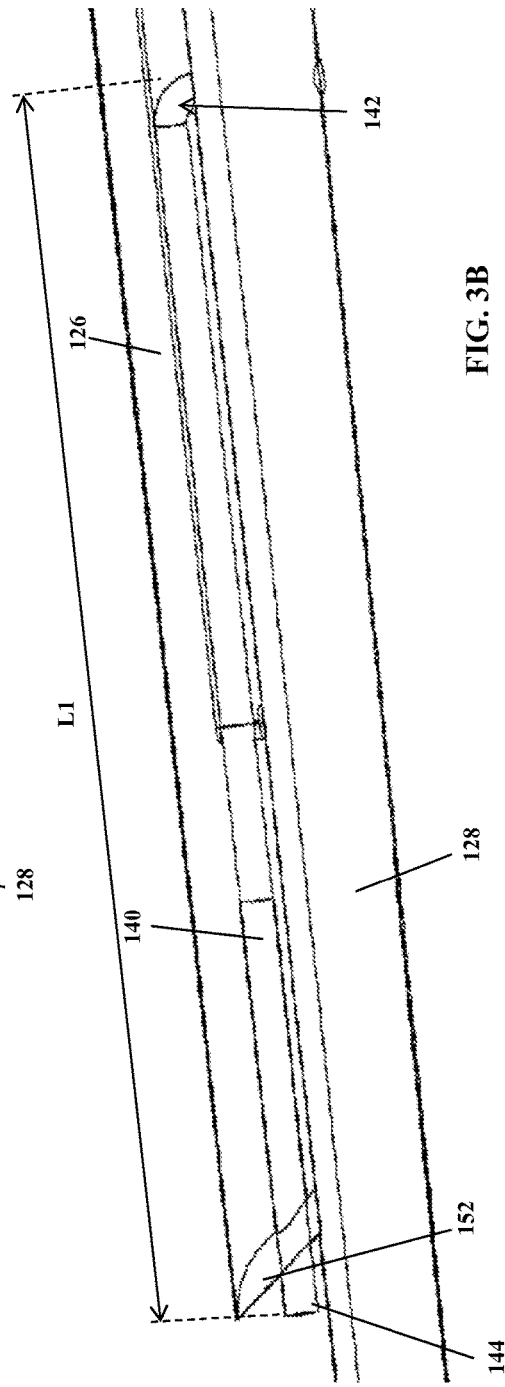
FIG. 3B is side view of the top rail portion in phantom showing the rod protruding from the first jaw in the open position.

As shown in FIG. 3A, the jaw portion 150 generally comprises a first jaw 152 on the distal end of the top rail portion 126, and a second jaw 154 on the distal end of the bottom rail portion 128. The first jaw 152 and the second jaw 154 longitudinally translate away from each other by operation of the handle 110 and the top rail portion 152 moving in the direction of arrow 127. The rod 140 is movably coupled with the first jaw 152 and the rod 140 is longitudinally disposed within the top rail portion 126, as shown in FIG. 3B. The rod 140 is longitudinally coupled within the bottom rail portion 128 by way of the proximal end 142. In one embodiment, the spring 130 is abuts the proximal end 142 of the rod 140 as shown in FIG. 6A. The rod 140 may be integrally formed with the bottom rail portion 128, or the rod 140 may be a separate piece or element. The jaw portion 150 includes a width of W1 when in the open position; such that the width W1 separates the first jaw portion 152 and the second jaw portion 154. The width W1 may be selected based upon the type of tissue to be removed. For example, the width W1 may between about 0.1 and 20 cm, or between about 2 and 100 cm. If small ligaments are to be removed, the width W1 may be smaller than about 5 cm. In one embodiment, the rod 140 includes a length L1, where the length L1 is greater the width W1, such that when the jaw portion 150 is in the open position and opens to a width W1, the distal end 144 of the rod 140 is able to protrude from the first jaw 152 and dislodge or detach any tissue attached to the first jaw. As such, the length L1 may between about 10 and 200 cm, or between about 200 and 1000 cm.

The ejector 160 is longitudinally movable within the bottom rail portion 128. The bottom rail portion 128 includes a grooved portion 132 to operably couple the ejector 160 within the bottom rail portion 128, as shown in FIGS. 4A-4B. The grooved portion 132 includes a seated recess 134 on the distal end. The seated recess 134 receives the cleaning post 164 from the ejector 160 and allows the cleaning post 164 to lay flat against exterior surface of the second jaw 154. The grooved portion 132 includes a longitudinal rail 136, as shown in FIGS. 7B & 7D, which receives the distal lip 190 on the top rail portion 126 and allows the top rail portion 126 to longitudinally translate with respect to the bottom rail portion 126 towards the pin 165 on the ejector 160. The longitudinal rail 136 and the distal lip 190 include a similar cross-sectional profile as to allow the distal lip 190 longitudinally translate along the longitudinal rail 136. Although the longitudinal rail 136 and the distal lip 190 are shown to have a rectangular cross-section, other cross-sections may be employed, such as a grooved or conical cross-section, a circular or elliptical cross-section, or other polygonal cross-section.

Figure 5A:
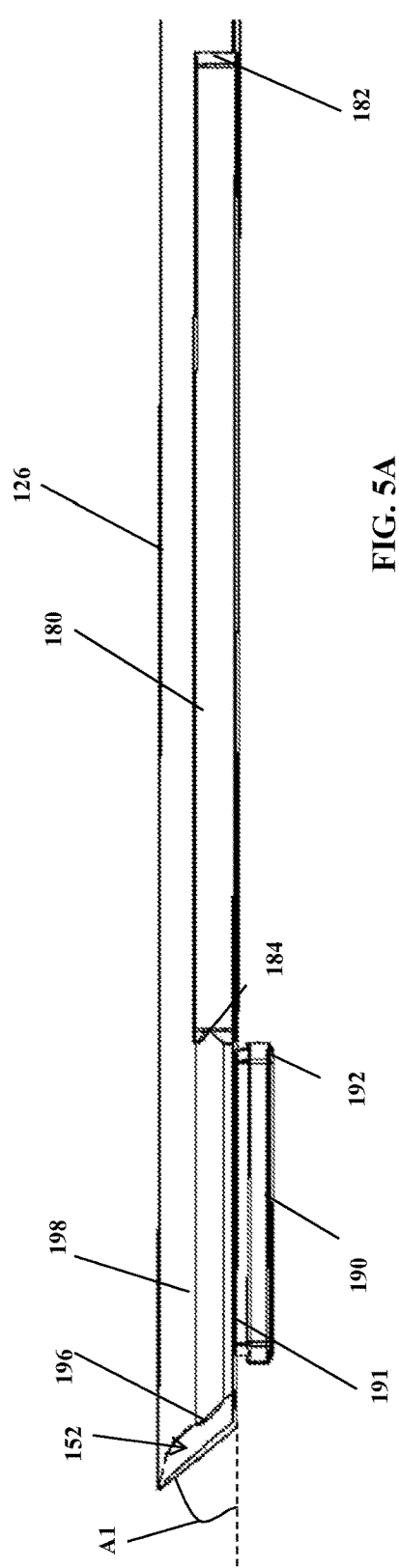
FIG. 5A is a side view of the top rail portion and the distal lip portion.
Figure 7A:
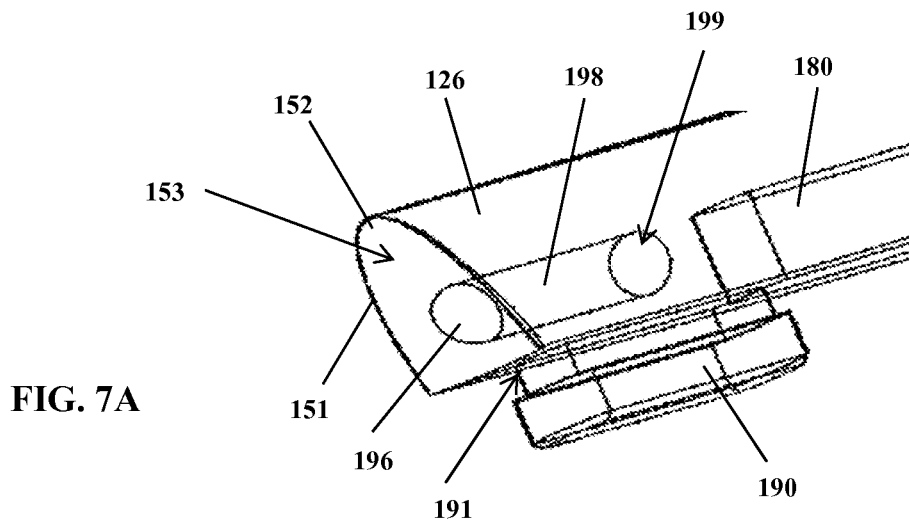
FIG. 7A is a perspective side view of the top rail portion.
Figure 7B:
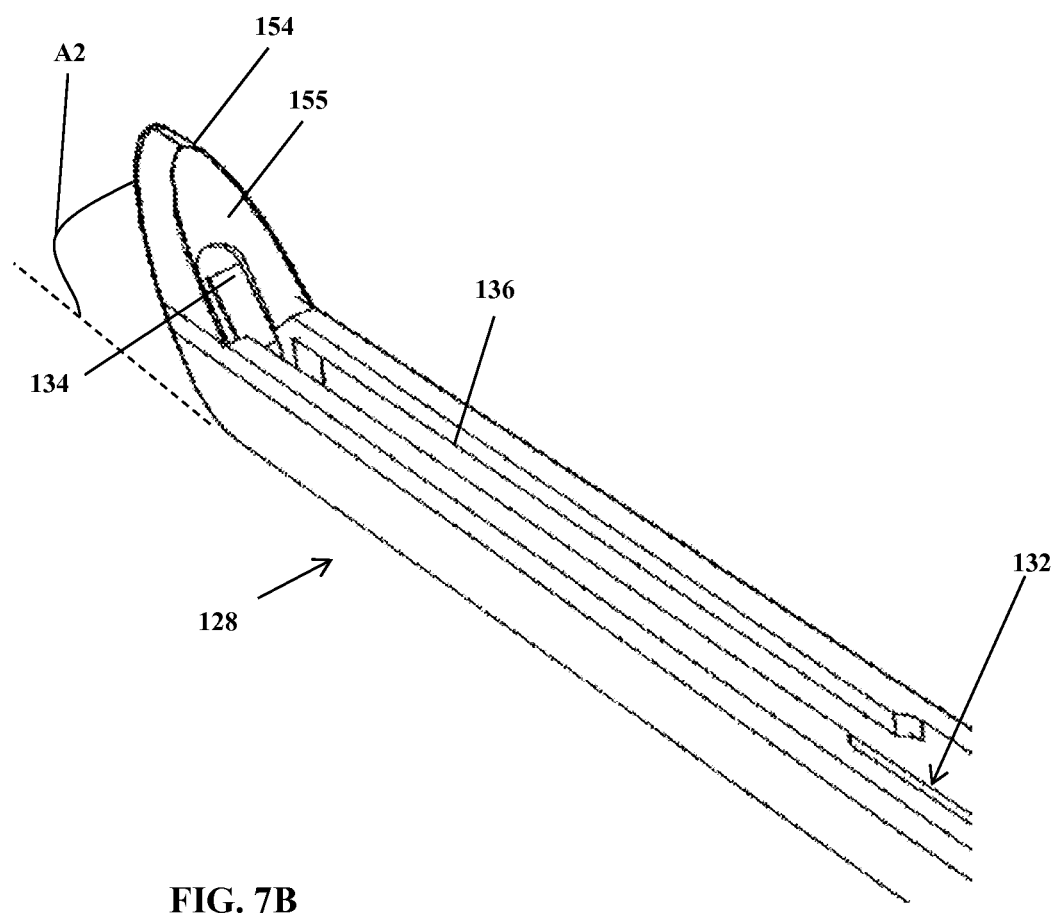
FIG. 7B is a perspective back view of the bottom rail portion.

As shown in FIG. 5A 7A, 7C, in one embodiment, the distal lip 190 includes a sliding member 191 that includes a width W2 that is smaller or narrower than the width of the distal lip 190. In one embodiment, the width W2 is smaller than the width W3 of the longitudinal rail 136, such that the sliding member 191 may longitudinally translate along the longitudinal rail 136. The grooved portion 132 includes a proximal recess portion 138 that is able to seat the spring 130 and the proximal end 142 of the rod 140. In one embodiment, the distal end of ejector 160 may traverse the longitudinal rail 136 as to further detach tissue engaged with the open position of the self-cleaning tissue removal instrument.

Figure 5B:
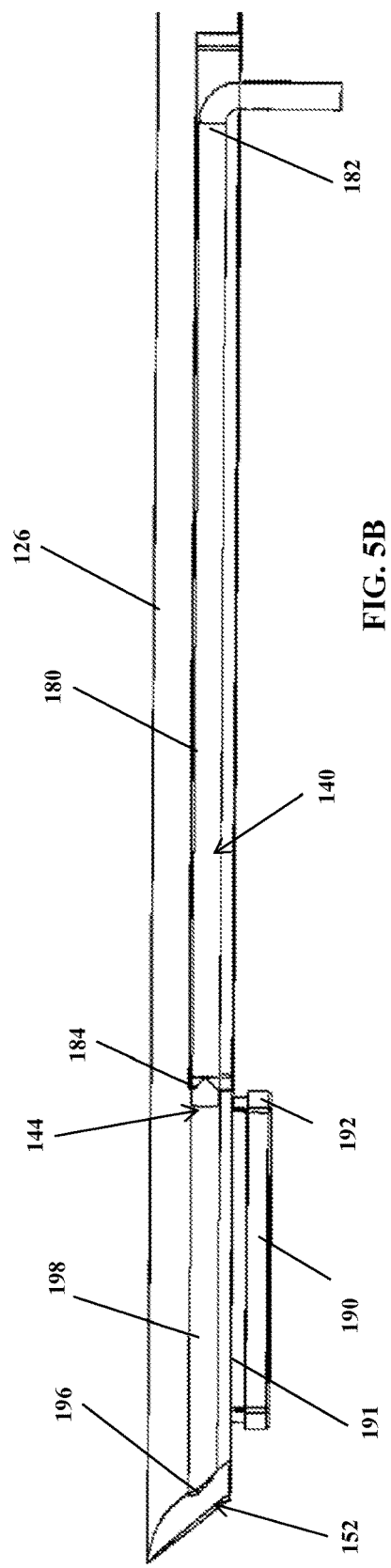
FIG. 5B is side view of the top rail portion shown in phantom and the rod disposed within the top rail portion.

The top rail portion 126 includes the first jaw 152 on the distal end and a longitudinal cavity 198 communicating with the first jaw 152, as shown in FIG. 5A. The longitudinal cavity 198 includes a distal opening 196 to communicate with the first jaw 152, as shown in FIG. 7A. The rod 140 is coaxially disposed within the longitudinal cavity 198 to allow the top rail portion 126 to be longitudinally moveable along the rod 140, and to allow the distal end 144 of the rod 140 to protrude out the distal opening 196 in the open position as to dislodge tissue stuck or adhered to the first jaw 152. The first jaw 152 is operably coupled to the distal end of the top rail portion 126 and is offset at an angle A1. The offset angle A1 substantially matches the offset angle of the second jaw 154, as further explained below. The offset angle A1 and A2 allows the first jaw 152 and the second jaw 154 to slice or cut tissue at an angle. The top rail portion 126 includes a grooved portion 180 to receive the middle and distal portions of the rod 140, as shown in FIG. 5B. The grooved portion 180 includes a distal opening 184 and a proximal end, whereby the distal end 144 of the rod 140 sits within the distal end 184 of the grooved portion 180 when the self-cleaning tissue removal instrument 100 is in the closed position.

As shown in FIG. 6A, the ejector 160 includes the pin 165 that projects within the grooved portion 132 of the bottom rail portion 126. The distal end 192 of the lipped portion 190 engages the pin 165 of the ejector 160 as to longitudinally translate the ejector 160 and pin 165 towards the proximal end of the self-cleaning tissue removal instrument 100. By translating the pin 165 towards the proximal end, the ejector 160 and the cleaning post 164 disengage from the seated recess 134. The lipped portion 190 may longitudinally translate the pin 165 a distance D1 sufficient to clean or remove tissue engaged on the second jaw portion 154 by longitudinal or axial movement of the cleaning post 164. The distance D1 may be selected based upon the type of tissue to be removed or cleaned from the second jaw portion 154. Distance D1 may be between about 0.1 and about 100 mm. The distance D1 may be at least 5 mm to disengage the cleaning post 164 from the second jaw portion 154.

As shown in FIG. 6A, the distal end 144 of the rod 140 protrudes from the first jaw portion 152 as to remove or clean any tissue that may be stuck or engaged to the face of the first jaw portion 152. The distal end 14 of the rod 140 may protrude from the first jaw portion 152 to a distance D2 sufficient to clean or remove tissue engaged on the first jaw portion 152 by longitudinal movement of the top rail portion 126 towards the proximal end of the self-cleaning tissue removal instrument. The distance D2 may be selected based upon the type of tissue to be removed or cleaned from the first jaw portion 152. Distance D2 may be between about 0.1 and about 100 mm. The distance D2 may be at least 5 mm to allow distal end 144 of the rod 140 to protrude from the first jaw portion 152. In one embodiment, the distance D1 is equal to the distance D2. In other embodiment, the distance D1 is greater than the distance D2. In another embodiment, the distance D1 is smaller than the distance D2.

As shown in FIG. 6B, the self-cleaning tissue removal instrument 100 is in the closed position and the first jaw 152 engages the second jaw 154 as to form a cupped portion 156 by which to remove tissue. The second jaw 154 may include a second cup portion 155 and the first jaw 152 may include a first cup portion 153 that substantially matches the second cup portion 155. In one embodiment, the first jaw 152 and the second jaw 154 include sharpened edges 151 surrounding the first and second cup portions 153 and 155, as shown in FIGS. 7A-7B. The sharpened edges 151 serve to gouge or cut tissue or bone. Alternatively, the grooved portion 156 may be surrounded by teeth or other sharpened features to assist in the removal of bone or tissue.

As shown in FIG. 7B, the second jaw 154 is operably coupled on the distal end of the bottom rail portion 128 and set an angle A2. The angle A2 may be selected to allow for the user to remove tissue or to engage tissue. The offset angle A2 substantially aligns and matches with the offset angle A1 of the first jaw 152 such that the cupped portion 156 seals together with the sharpened edges 151 of the first jaw 152 and the second jaw 154 align in the closed position as shown in FIG. 6B. The bottom rail portion 128 includes the seated recess 134 on the distal end and within the second jaw 154. The seated recess 134 receives the cleaning post 164. The seated recess 134 is also offset from the longitudinal axis at an angle A2, such that the seated recess 134 substantially aligns with the second cup portion 155 of the second jaw 154.

In an alternative embodiment, the ejector 160 may rotate about its middle portion as to disengage the cleaning post 164 from the seated recess 134, as shown in FIG. 6C. As the top rail portion 126 is longitudinally translated towards the proximal end, the distal lip portion 190 pushes the pin 165 on the ejector 160 away from the longitudinal axis as to rotate the ejector 160 in the direction of arrow 161, as shown in FIG. 6D, and move the cleaning post 164 away from the second jaw portion 154 as to clean and disengage any tissue that may be stuck on the second jaw portion 154. In this embodiment, the ejector 160 operates as a lever mechanism and rotates about a pin 163 that is operably coupled with the grooved portion 132 of the bottom rail portion. The distal lip portion 190 may include an exterior face 194 that slides over the top of the pin 165 as the top rail portion 126 is translated towards the proximal end. The proximal end 162 of ejector 160 may be coupled with a spring as to bias the ejector 160 and the cleaning post 164 to seat within the seated recess 134. The proximal end 162 of the ejector 160 rotates within the grooved portion 132 of the bottom rail portion, such that the grooved portion 132 includes sufficient space for the proximal end 162 to rotate and displace the cleaning post 164 from the seated recess 134. The degree of rotation of the ejector 160 in the lever mechanism may be between about 0.1 to about 20.0 degrees. The degree of rotation of the ejector 160 may be adjusted depending on the type of tissue to be removed from the seated recess 164. For example, the ejector 160 may be rotated to about 10 or more degrees to remove substantially large tissue or connective tissue.

If the ejector 160 operates by way of the lever mechanism, the ejector 160 may include a curvature along its longitudinal axis, as shown in FIG. 6E. The curvature may include an angle A4, where A4 is between about 0.1 to about 20.0 degrees. The selection of the angle A4 may be optimized or adjusted depending on the amount or type of tissue to be removed. For example, the angle A4 may be greater than 10 degrees if the cleaning post 164 is to remove substantial tissue or connective tissue that might stick to the cleaning post 164, whereby the cleaning post 164 is removed from the seated recess by more 10 degrees. The grooved portion 130 may also include an angle of curvature to match the angle of curvature A4 of the ejector 160 to allow sufficient rotation of the ejector 160 about pin 163. And the size of the pin 165 may be selected to increase or decrease the lever rotation of the ejector 160.

FIG. 6F shows the distal lip 190 engaged with the pin 165 of the ejector 160 for the curved embodiment of the ejector. The distal lip 190 includes the exterior face 194 having a curvature at angle A5, where A5 is between about 0.1 to about 20.0 degrees. The selection of the angle A5 may be substantially the same as the angle A4 of the ejector 160 and may be optimized or adjusted depending on the amount or type of tissue to be removed. For example, the angle A5 may be greater than 10 degrees if the cleaning post 164 is to remove substantial tissue or connective tissue that might stick to the cleaning post 164, whereby the cleaning post 164 is removed from the seated recess by more 10 degrees.

As shown in FIG. 8A, the ejector 160 includes the cleaning post 164 on the distal end and the pin 126 on the middle portion, and the spring 130 on the proximal end. The spring 130 on the proximal end of the ejector 160 biases the ejector 160 towards its distal end. In one embodiment, the cleaning post 164 is offset from the longitudinal axis at angle A3, as shown in FIG. 8B, such that the angle A3 is the same as Angle A2 and the cleaning post 164 may substantially align and sit within the seated recess. In one embodiment, the cleaning post 164 includes a tongue portion 166 on the face of the cleaning post 164. The tongue portion 166 may slightly offset or angled from the cleaning post 164, and may provide additional cleaning engagement portions for the cleaning post 164. In one embodiment, the tongue portion 166 may include a shape memory material, whereby once the tissue is engaged by or stuck to the second jaw portion 154, the shape memory material may transition from a first state to a second state by operation of temperature or pressure as to disengage or move the tissue from away the second jaw portion 154. The second state may be selected depending upon the type of tissue being removed, such as the temperature of the tissue or the pressure of the tissue exerts on the self-cleaning tissue removal instrument. In this embodiment, the operation or movement of the ejector may be unnecessary since the tongue portion 166 may tent up from a flatten state as to clean the surface of the second jaw portion 154. Shape memory materials may include shape memory alloys or shape memory polymers. A variety of alloys exhibit the shape-memory effect. Alloying constituents can be adjusted to control the transformation temperatures of the shape memory alloys. Some common systems include the following, but not limited to: Ag—Cd 44/49 at. % Cd; Au—Cd 46.5/50 at. % Cd; Cu—Al—Ni 14/14.5 wt % Al and 3/4.5 wt % Ni; Cu—Sn approx. 15 at % Sn; Cu—Zn 38.5/41.5 wt. % Zn; Cu—Zn—X (X=Si, Al, Sn); Fe—Pt approx. 25 at. % Pt; Mn—Cu 5/35 at % Cu; Fe—Mn—Si; Co—Ni—Al; Co—Ni—Ga; Ni—Fe—Ga; Ti—Nb; Ni—Ti approx. 55-60 wt % Ni; Ni—Ti—Hf; Ni—Ti—Pd; Ni—Mn—Ga. Shape memory polymers include thermoplastic and thermoset (covalently cross-linked) polymeric materials. Shape memory polymers are known to be able to store up to three different shapes in memory. Shape memory polymers have demonstrated recoverable strains of above 800%. In another embodiment, the distal end 144 of the rod 140 may include a shape memory material, whereby once the tissue is engaged or stuck to the first jaw portion 152, the shape memory material may transition from a first state to a second state by operation of temperature or pressure as to disengage or move the tissue from the first jaw portion 152. In this embodiment, the operation or movement of the rod may be unnecessary since the distal end of rod may tent up from a flatten state as to clean the surface of the second jaw portion 154.

As shown in FIG. 9A, the rod 140 includes a substantially tubular member, although the rod 140 may assume any polygonal, circular, or elliptical member. The proximal end 140 includes a substantially perpendicular section 146, such that the proximal end of the spring 130 may abut the proximal end 140. Alternatively, the substantially perpendicular section 146 may be a separate element from the rod 140 and may be incorporated into the bottom rail portion 128.

As shown in FIG. 9B, the bottom rail portion 128 may be integral with the second handle 114 or may be a separate piece or element. The second handle 114 includes an opening 118 to engage the pin 116, as to allow the first handle to rotate about the opening 118. The second handle 114 may include a general arcuate or curved shape for ease of grip and use by an operator. The second handle 114 may be generally stationary with respect to the first handle 112. In one embodiment, the second handle 114 includes a wishbone spring to bias the first handle 112 distally away from the second handle 114 and the open position of the self-cleaning tissue removal instrument 100.

Figure 9C:
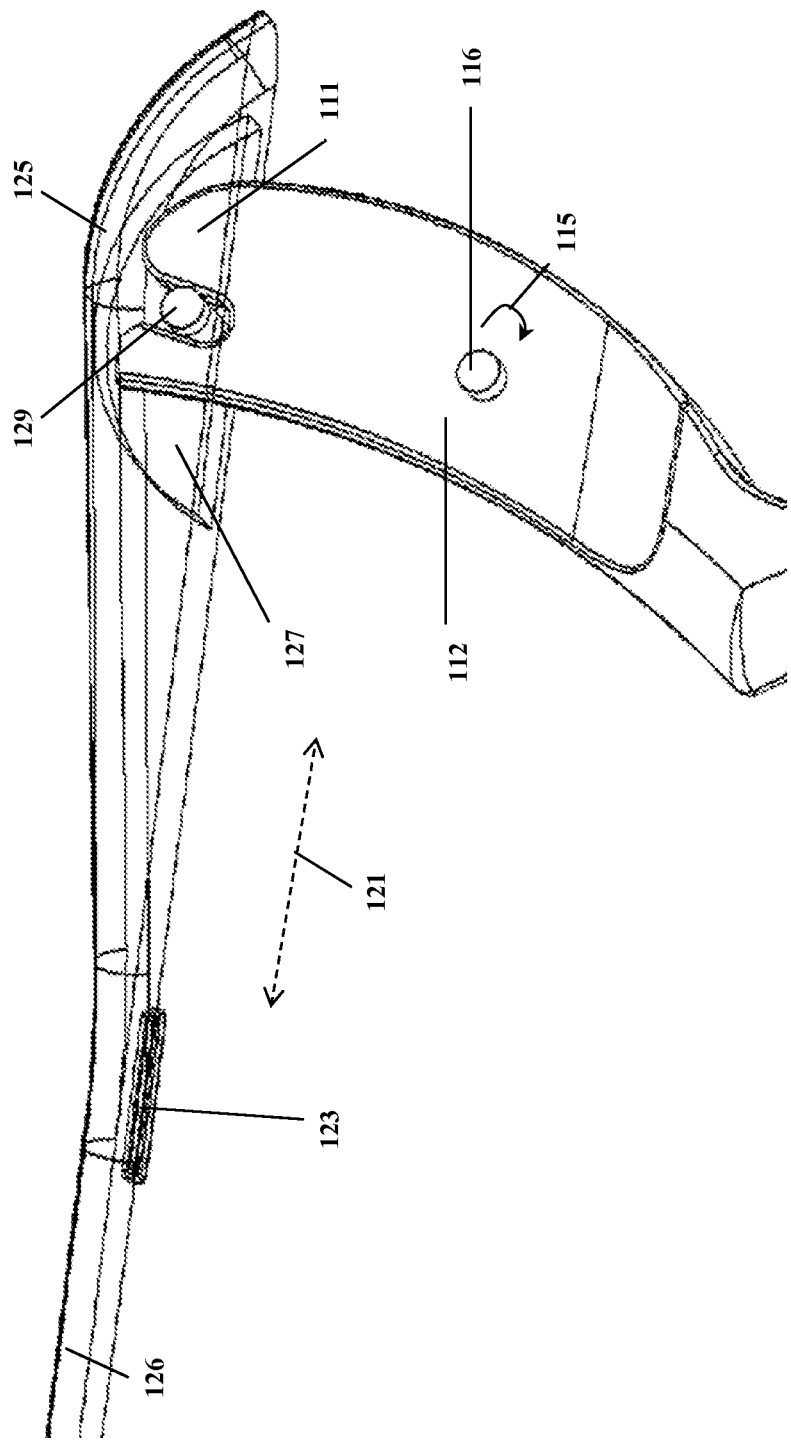
FIG. 9C is a perspective side view of the first handle and the top rail portion shown in the phantom.

As shown in FIG. 9C, the top rail portion 126 includes a proximal end 125 that is operably coupled with the first handle 112. The proximal end 125 includes a slotted region 127 to receive the distal end 111 of the first handle 112. The slotted region 127 includes pin 129 operably coupled to the distal end 111 of the first handle 112, as to longitudinally translate the top rail portion 126 in the direction of arrow 121. The first handle 112 rotates about pin 116 in the direction of arrow 115 as to longitudinally translate the proximal end 125 of the top rail portion 125. In one embodiment, the top rail portion 126 may include a proximal lip portion 123 to engage with a grooved portion on the bottom rail portion 128 and to assist with the longitudinal stabilization of the top rail portion 126 during the translation from the open position to the closed position.

Figure 9D:
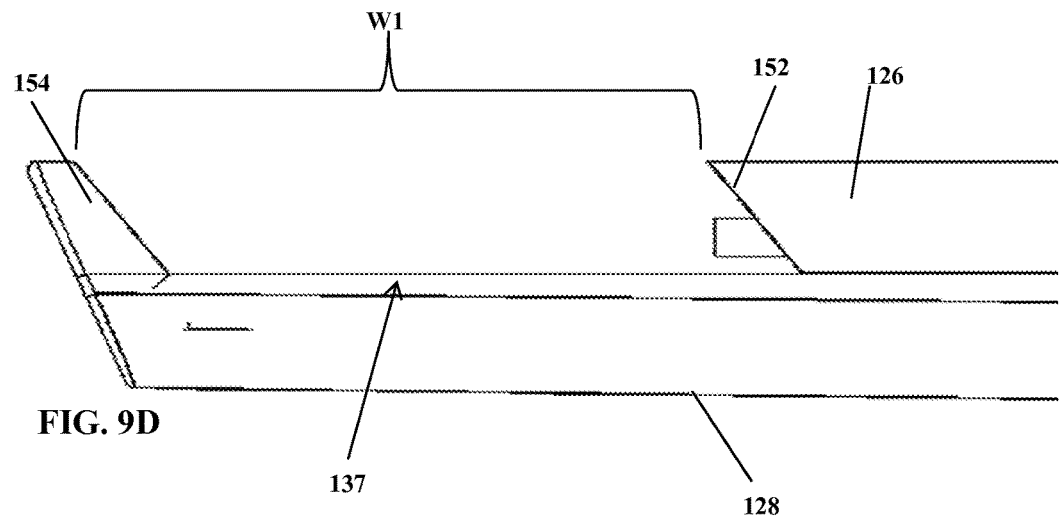
FIG. 9D is a side view of an alternative embodiment of the bottom rail portion including a shape memory material and the top rail portion in the open position.
Figure 9E:
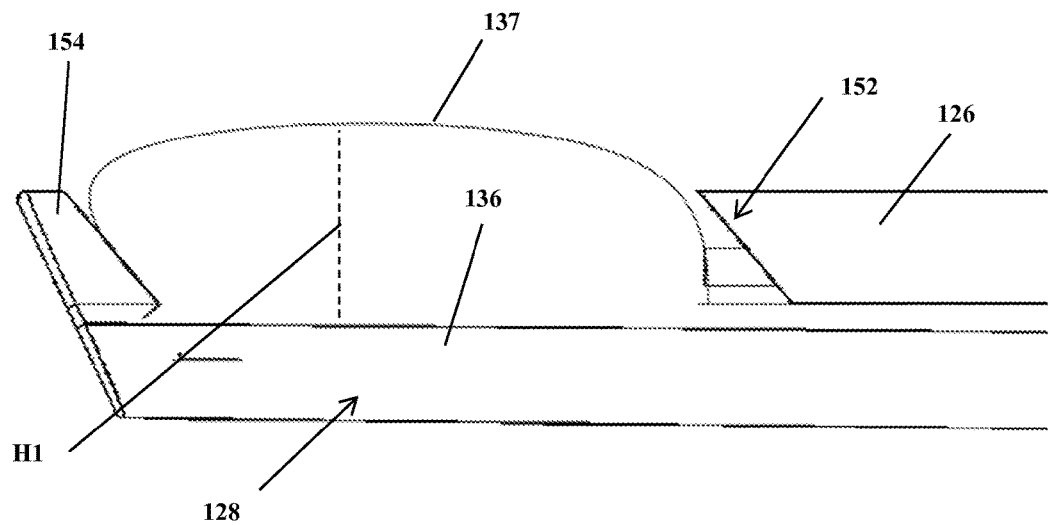
FIG. 9E is a side view of an alternative embodiment of the bottom rail portion including a shape memory material in the tented position and the top rail portion in the open position.

FIG. 9D shows an alternative embodiment of the self-cleaning tissue removal instrument 100. The bottom rail portion 128 includes a layer 137 of shape memory material disposed on top of the longitudinal rail and traversing the width W1 of the open position. The shape memory material may transition a first state to a second state by operation of temperature or pressure as to disengage or move the tissue from away the width W1, as shown in FIG. 9E. The second state may be selected depending upon the type of tissue being removed, such as the temperature of the tissue or the pressure of the tissue exerts on the self-cleaning tissue removal instrument. The layer 137 of shape memory material includes a height H1 in the second state, which may detach or disengage tissue stuck between the first jaw 152 and the second jaw 154. Height H1 may be selected to be higher than the top of the top rail portion 152. The layer 137 of shape memory material may transition to the second state as to remove tissue engaged on the first jaw 152 and the second jaw 154, such that the layer 137 of shape memory material traverses the exterior surface of the first jaw 152 and second jaw 154. The layer 137 of shape memory material may be additional to the ejector 160 and rod 140, or may operate by itself as the cleaning mechanism. Shape memory materials may include shape memory alloys or shape memory polymers. A variety of alloys exhibit the shape-memory effect. Alloying constituents can be adjusted to control the transformation temperatures of the shape memory alloys. Some common systems include the following, but not limited to: Ag—Cd 44/49 at. % Cd; Au—Cd 46.5/50 at. % Cd; Cu—Al—Ni 14/14.5 wt % Al and 3/4.5 wt % Ni; Cu—Sn approx. 15 at % Sn; Cu—Zn 38.5/41.5 wt. % Zn; Cu—Zn—X (X=Si, Al, Sn); Fe—Pt approx. 25 at. % Pt; Mn—Cu 5/35 at % Cu; Fe—Mn—Si; Co—Ni—Al; Co—Ni—Ga; Ni—Fe—Ga; Ti—Nb; Ni—Ti approx. 55-60 wt % Ni; Ni—Ti—Hf; Ni—Ti—Pd; Ni—Mn—Ga. Shape memory polymers include thermoplastic and thermoset (covalently cross-linked) polymeric materials. Shape memory polymers are known to be able to store up to three different shapes in memory. Shape memory polymers have demonstrated recoverable strains of above 800%.

Figure 10:
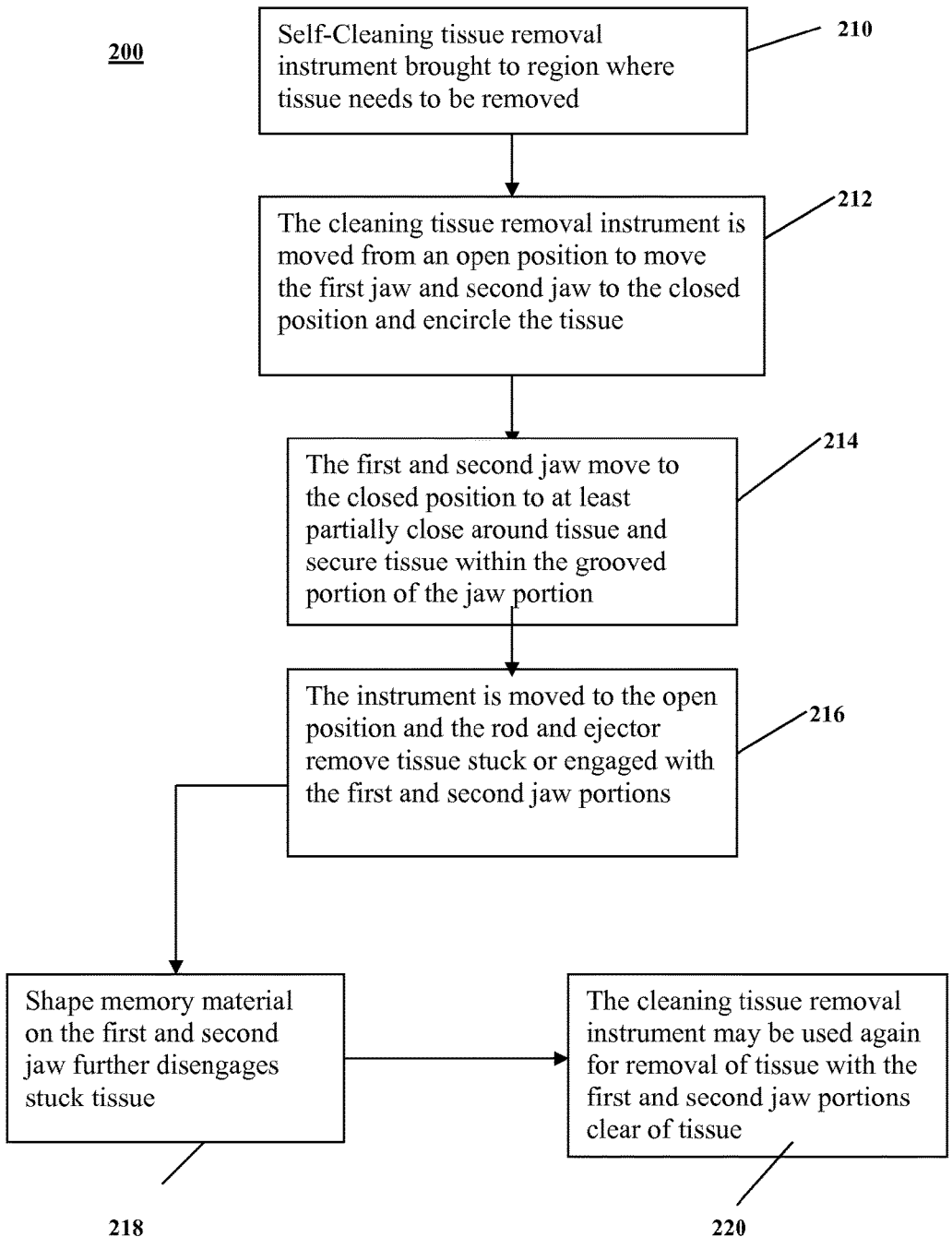
FIG. 10 is a flow chart for the method of using the self-cleaning tissue removal instrument.

FIG. 10 generally shows the method of removing tissue or bone by the self-cleaning tissue removal instrument 200. The self-cleaning tissue removal instrument is brought to a region of tissue to be removed in step 210. Then the first jaw and second jaw move from the open position and to the closed position and are placed around a portion of the tissue to be removed in step 212. Then the first and second jaws move to the closed position to at least partially close around tissue and secure tissue within the grooved portion of the jaw portion in step 214. The self-cleaning tissue removal instrument may then be moved to the open position and the rod and ejector remove tissue stuck or engaged with the first and second jaw portions in step 216. In one embodiment, shape memory material on the first and the second jaw may transition to a second state to remove stuck tissue from the first and second jaw portions in step 218. Then cleaning tissue removal instrument may be used again for removal of tissue with the first and second jaw portions clear of tissue in step 220.

As can be understood by one skilled in the art, the self-cleaning tissue removal instrument 100 and/or any of its components may have any size, shape, length, thickness, height, weight, or any other parameters. Such parameters may be selected by the surgeon (or other qualified professional) for performance of specific procedures. Further, the self-cleaning tissue removal instrument 100 and/or any of its components may be manufactured from metal, plastic, synthetic material, or other suitable materials, or any combination thereof. In one embodiment, the self-cleaning tissue removal instrument 100 is composed of a metal alloy, titanium, nitinol, or stainless steel, or alternatively, any medical grade composite or ceramic.

In some embodiments, various lengths and configurations may also include various features to accommodate different applications for the self-cleaning tissue removal instrument 100. The self-cleaning tissue removal instrument 100 can be constructed of various materials to aid in radio translucency, strength, flexibility, and integration with anatomy, etc.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A self-cleaning tissue removal instrument comprising:
a handle operably coupled with a proximal end of a rail portion;
a jaw portion operably coupled to a distal end of the rail portion, a longitudinal axis running along the proximal end to the distal end of the self-cleaning tissue removal instrument;
wherein the jaw portion is moved from an open position to a closed position by operation of the rail portion translating along the longitudinal axis of the self-cleaning tissue removal instrument, and the jaw portion clamps down and removes tissue in the closed position; and
a cleaning mechanism operably coupled with the rail portion, whereby the cleaning mechanism disengages any tissue attached to the jaw portion when the jaw portion longitudinally translates to the open position;
wherein the rail portion includes a top rail portion operably coupled with a bottom rail portion; and the cleaning mechanism operably coupled between the top rail portion and the bottom rail portion, whereby the top rail portion longitudinally translates along the longitudinal axis to the open position of the jaw portion;
wherein the handle operates to open the jaw portion and longitudinally translate the top rail portion from the open position to the closed position; and the handle includes a first handle rotatably coupled with a second handle by way of a pin;
wherein the first handle is operably coupled with the bottom rail portion and the second handle is operably coupled with the top rail portion; and the second handle rotates about the first handle to longitudinally translate the top rail portion to the open position;
wherein the cleaning mechanism further comprises an ejector operably coupled with a distal end of the bottom rail portion, a spring operably coupled to a proximal end of the ejector, and a rod operably coupled with a distal end of the top rail portion, wherein the ejector and the rod operate to remove tissue disposed within the jaw portion;
wherein the ejector includes a distal end and a cleaning post on the distal end to remove punched tissue from the jaw portion; the rod includes a proximal end with a substantially right angle with respect to a distal end; the top rail portion includes a grooved inner surface as to receive the rod and to allow the top rail portion to longitudinally translate along the rod; the top rail portion includes a distal lip portion to engage the bottom rail portion as to be able to longitudinally translate on top of the bottom rail portion; and the ejector includes a pin disposed on a middle portion of the ejector;

wherein the jaw portion further comprises a first jaw on the distal end of the top rail portion, and a second jaw on the distal end of the bottom rail portion, whereby the first jaw and the second jaw longitudinally translate away from each other by rotation of the second handle; the rod is movably coupled with the first jaw and the rod is longitudinally disposed within the top rail portion; and the proximal end of the rod is disposed within the bottom rail portion, and the spring abuts the proximal end of the rod;

wherein jaw portion includes a width of W1 when in the open position; such that the width W1 separates the first jaw portion and the second jaw portion; the rod includes a length L1, where the length L1 is greater than the width W1; and the width W1 may be between 0.1 and 20 cm;

wherein the bottom rail portion includes a grooved portion to operably couple the ejector within the bottom rail portion; the ejector is longitudinally movable within the grooved portion; the grooved portion includes a seated recess on a distal end; the seated recess receives the cleaning post from the ejector and allows the cleaning post to lay flat against an exterior surface of the second jaw; and the grooved portion includes a longitudinal rail that receives the distal lip from the top rail portion and allows the top rail portion to longitudinally translate along the longitudinal rail towards the pin on the ejector;

wherein the distal lip includes a sliding member that includes a width W2 that is smaller or narrower than a width W3 of the longitudinal rail and a width of the distal lip; and the grooved portion includes a proximal recess portion that is able to seat the spring and the proximal end of the rod; and wherein the top rail portion further comprises a longitudinal cavity and a distal opening communicating with the first jaw; the rod is coaxially disposed within the longitudinal cavity to allow the top rail portion to be longitudinally moveable along the rod, and to allow the distal end of the rod to protrude out the distal opening in the open position as to detach tissue adhered to the first jaw; the top rail portion includes a grooved portion to receive the middle and distal portions of the rod; the grooved portion includes a distal opening and a proximal end, whereby the distal end of the rod sits within the distal end of the grooved portion when the self-cleaning tissue removal instrument is in the closed position.

2. The self-cleaning tissue removal instrument of claim 1, wherein a distal end of the lipped portion engages the pin of the ejector as to longitudinally translate the ejector and pin towards the proximal end of the self-cleaning tissue removal instrument and disengage the cleaning post from the seated recess; the lipped portion may longitudinally translate the pin a distance D1 sufficient to detach tissue engaged on the second jaw portion by movement of the cleaning post; wherein the distance D1 may be between 0.1 and 100 mm; and the distal end of the rod may protrude from the first jaw portion to a distance D2 sufficient to detach tissue engaged on the first jaw portion by longitudinal movement of the top rail portion towards the proximal end of the self-cleaning tissue removal instrument; the distance D2 may be between 0.1 and 100 mm.

3. The self-cleaning tissue removal instrument of claim 2, wherein the second jaw includes a second cup portion and the first jaw includes a first cup portion that substantially matches the second cup portion such that when the first jaw engages the second jaw a cupped portion in the closed position is formed to remove the tissue; and the first jaw and the second jaw include sharpened edges surrounding the first and second cup portions.

4. The self-cleaning tissue removal instrument of claim 2, wherein the cleaning post includes a tongue portion on the face of the cleaning post; wherein the tongue portion includes a shape memory material; the shape memory material transitions from a first state to a second state by operation of temperature or pressure as to disengage or move the tissue from away the second jaw portion.

5. The self-cleaning tissue removal instrument of claim 2, wherein the second handle includes an opening to engage the pin, as to allow the first handle to rotate about the opening; wherein the second handle includes a wishbone spring to bias the first handle distally away from the second handle and to the open position.

6. The self-cleaning tissue removal instrument of claim 2, wherein the top rail portion includes a proximal end that is operably coupled with the first handle; the proximal end includes a slotted region to receive the distal end of the first handle; the slotted region includes a pin operably coupled to the distal end of the first handle, as to longitudinally translate the top rail portion; and the first handle rotates about pin; and the top rail portion includes a proximal lip portion to engage with a grooved portion on the bottom rail portion to assist with the longitudinal stabilization of the top rail portion during the translation from the open position to the closed position.

7. The self-cleaning tissue removal instrument of claim 1, wherein the bottom rail portion includes a grooved portion to operably couple the ejector within the bottom rail portion; the grooved portion includes a seated recess on a distal end; the seated recess receives the cleaning post from the ejector and allows the cleaning post to lay flat against an exterior surface of the second jaw; the ejector operates as a lever mechanism and rotates about a pin that is operably coupled with the grooved portion of the bottom rail portion; as the top rail portion is longitudinally translated towards the proximal end, the distal lip portion pushes the pin on the ejector away from the longitudinal axis as to rotate the ejector and move the cleaning post away from the second jaw portion as to detach any tissue on the second jaw portion; and the degree of rotation of the ejector is between 0.1 to 20.0 degrees.

8. A method of using a self-cleaning tissue removal instrument of claim 4, comprising:
    moving a first jaw towards a second jaw from an open position to the closed position around a portion of tissue to be removed;
    moving the first jaw to the open position and a rod and an ejector detaching tissue engaged with the first jaw and second jaw;
    transitioning a shape memory material on the first and the second jaw to a second state to further detach tissue engaged on the first jaw and second jaw.

9. The self-cleaning tissue removal instrument of claim 7, wherein the ejector includes a curvature along its longitudinal axis, wherein the curvature includes an angle A4 between 0.1 to 20.0 degrees.

10. A self-cleaning tissue removal instrument comprises:
    a handle operably coupled with a proximal end of a rail portion, the rail portion includes a top rail portion operably coupled with a bottom rail portion, the handle includes a first handle operably coupled with the bottom rail portion and a second handle is operably coupled with the top rail portion;
    a jaw portion operably coupled to a distal end of the rail portion, a longitudinal axis running along the proximal end to the distal end of the self-cleaning tissue removal instrument; wherein the jaw portion is moved from an open position to a closed position by operation of the rail portion translating along the longitudinal axis of the self-cleaning tissue removal instrument, and the jaw portion clamps down and removes tissue in the closed position, the jaw portion further comprises a first jaw on a distal end of the top rail portion, and a second jaw on a distal end of the bottom rail portion, whereby the first jaw and the second jaw longitudinally translate away from each other by rotation of the second handle; a rod is movably coupled with the first jaw and the rod is longitudinally disposed within the top rail portion; and a proximal end of the rod is disposed within the bottom rail portion, and a spring is abuts the proximal end of the rod;

a cleaning mechanism operably coupled with the rail portion, the cleaning mechanism comprises an ejector operably coupled with the distal end of the bottom rail portion, a spring operably coupled to a proximal end of the ejector, and a rod operably coupled with the distal end of the top rail portion, wherein the ejector and the rod operate to remove tissue disposed within the jaw portion;

the ejector includes a distal end and a cleaning post on the distal end to remove punched tissue from the jaw portion; the rod includes a proximal end with a substantially right angle with respect to a distal end; the top rail portion includes a grooved inner surface as to receive the rod and to allow the top rail portion to longitudinally translate along the rod; the top rail portion includes a distal lip portion to engage the bottom rail portion as to be able to longitudinally translate on top of the bottom rail portion; and the ejector includes a pin disposed on a middle portion of the ejector; and the second handle rotates about the first handle to longitudinally translate the top rail portion to the open position and the handle; wherein the top rail portion further comprises a longitudinal cavity and a distal opening communicating with the first jaw; the rod is coaxially disposed within the longitudinal cavity to allow the top rail portion to be longitudinally moveable along the rod, and to allow the distal end of the rod to protrude out the distal opening in the open position as to detach tissue adhered to the first jaw; the top rail portion includes a grooved portion to receive the middle and distal portions of the rod; the grooved portion includes a distal opening and a proximal end, whereby the distal end of the rod sits within the distal end of the grooved portion when the self-cleaning tissue removal instrument is in the closed position.

* * * * *